(12) United States Patent
Southard

(10) Patent No.: US 7,319,038 B2
(45) Date of Patent: Jan. 15, 2008

(54) SENSOR FOR MONITORING AN ANALYTE

(75) Inventor: Glen E. Southard, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 762 days.

(21) Appl. No.: 10/664,314

(22) Filed: Sep. 17, 2003

(65) Prior Publication Data
US 2004/0072359 A1   Apr. 15, 2004

Related U.S. Application Data

(60) Provisional application No. 60/412,021, filed on Sep. 19, 2002.

(51) Int. Cl.
G01N 33/00 (2006.01)
G01N 21/78 (2006.01)

(52) U.S. Cl. .......................... 436/111; 436/20; 436/106; 436/164; 436/169; 436/177; 422/55; 422/56; 422/58; 422/61; 422/68.1; 422/101; 426/232; 116/206; 526/240; 526/330; 526/346; 526/319

(58) Field of Classification Search .................. 436/1, 436/20, 21, 106, 111, 73, 84, 164, 166, 169, 436/175, 177; 422/55, 56, 58, 61, 100, 101, 422/68.1; 426/232; 116/206; 526/240, 526/330, 346, 319
See application file for complete search history.

(56) References Cited

U.S. PATENT DOCUMENTS 3,067,015 A * 12/1962 Lawdermilt .................. 422/56

(Continued)

FOREIGN PATENT DOCUMENTS

| JP | 55141199 | * 11/1980 |
| JP | 358141798 | * 8/1983 |
| JP | 360188096 | * 9/1985 |
| WO | 01/77667 | * 10/2001 |
| WO | 01/77672 | * 10/2001 |
| WO | 01/77884 | * 10/2001 |

OTHER PUBLICATIONS

Suslick et al. Artificial Chemical Sensing: Olfaction and the Electronic Nose, 2001, pp. 8-14.*

(Continued)

Primary Examiner—Maureen M. Wallenhorst
(74) Attorney, Agent, or Firm—Francis A. Cooch

(57) ABSTRACT

A food spoilage sensor of the general formula

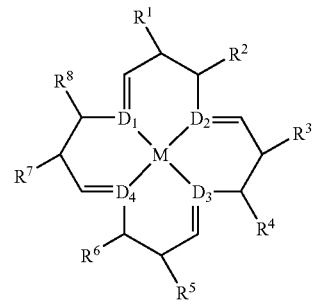

wherein M is a transition metal ion; $D_1$, $D_2$, $D_3$ and $D_4$ can be the same or different and can be N or P; $R^1$ and $R^2$, $R^3$ and $R^4$, $R^5$ and $R^6$, and $R^7$ and $R^8$ can be the same or different and from, taken together with the adjacent carbon atoms to which they are bonded and joined together, an aromatic or a cyclic group with at least one of the aromatic or cyclic groups possessing one or more polymerizable moieties. The complex selectively binds biogenic amines which are released by food spoilage microorganisms and undergo a detectable color change upon exposure thereto.

68 Claims, 4 Drawing Sheets

U.S. PATENT DOCUMENTS

| | | | | |
|---|---|---|---|---|
| 4,001,212 A | * | 1/1977 | Richman | 540/474 |
| 5,653,941 A | * | 8/1997 | Veretto et al. | 422/58 |
| 6,593,142 B2 | * | 7/2003 | Kelly et al. | 436/1 |
| 6,924,147 B2 | * | 8/2005 | Kelly et al. | 436/1 |
| 7,014,816 B2 | * | 3/2006 | Miller et al. | 422/87 |
| 2003/0003593 A1 | * | 1/2003 | Wallach | 436/170 |
| 2003/0104609 A1 | * | 6/2003 | Kalivretenos | 435/287.1 |

OTHER PUBLICATIONS

Blixt et al. International Journal of Food Microbiology, vol. 46, 1999, pp. 123-134.*

Kang et al. Chem. Commuications, 1999, pp. 93-94.*

* cited by examiner

SENSOR FOR MONITORING AN ANALYTE

CROSS-REFERENCE TO RELATED APPLICATIONS

This application claims the benefit of prior filed co-pending U.S. Provisional Application No. 60/412,021, filed Sep. 19, 2002, the contents of which are incorporated herein by reference.

BACKGROUND OF THE INVENTION

1. Field of the Invention

The present invention generally relates to a sensor having selective binding affinity for an analyte which is indicative of, for example, food spoilage.

2. Description of the Related Art

Food spoilage such as meat and fish spoilage occurs as bacteria begin to grow unchecked following respiration and circulation cessation at the time of slaughter. One of the markers of meat spoilage is the decarboxylation of free amino acids on and in the meat by enzymes released by spoilage microorganisms. Two of these products, putrescine and cadaverine, are particularly distinctive in odor, correlate well with surface bacterial counts, and are widely used to evaluate meat freshness both by trained meat inspectors and the individual consumers. Another product, histamine, is of interest due to its apparent ability to potentiate histamine intoxication, a form of food poisoning associated with the consumption of spoiled fish.

To detect the occurance of meat spoilage, sensors, e.g., polymeric sensors, have been developed. Polymeric sensors are typically prepared by ionically or covalently attaching an atomic, ionic, or molecular site to a polymer that, upon association with a particular analyte, will exhibit a detectable change in a measurable physical property. Exemplary measurable physical properties include spectroscopic (i.e., electronic absorbance or luminescence), electrochemical, or magnetic properties. The change in the physical property then provides a probe for the presence or absence of the associated analyte that can be measured using appropriate instrumentation or by direct observation. The polymer provides a support matrix that serves to immobilize the sensor sites and provide a localized density of the sensor sites as a means of optimizing detection of the analyte.

Molecular imprinting essentially involves making a polymer cast of a target molecule. The process of making the polymer cast involves dissolving the target molecule to be imprinted in a suitable solvent. Normally, a co-monomer, cross-linking monomer and a polymerization initiator are added to the reaction mixture. Radiation (photochemical or ionizing), thermal energy, or a chemical initiator is then applied to the reaction mixture to drive the polymerization process, ultimately resulting in the formation of a solid polymer. The resulting polymer may be processed using conventional polymer processing technologies, assuming those processes do not alter the structure of the molecularly imprinted sites. The imprinted molecule is extracted using methods appropriate for dissociating the target molecule from the polymer. Details of target molecule dissociation from the polymer are dependent upon the nature of the chemical interaction between the target molecule and the polymer binding site. The polymer dissociated from the target molecule possesses binding sites optimized for the structural and electronic properties of the target molecule. U.S. Pat. No. 5,110,833 describes the preparation of synthetic enzymes and synthetic antibodies by molecular imprinting techniques.

U.S. Pat. No. 6,593,142 discloses a polymeric food spoilage sensor wherein a polyazamacrocyclic transition metal complex selectively binds biogenic amines, such as cadaverine, putrescine and histamine, which are released by food spoilage microorganisms. The polymer then undergoes a detectable color change upon exposure to the biogenic amine, thus indicating that food spoilage has probably occurred. However, the polyazamacrocyclic transition metal complexes react slowly with cadaverine such that it can take several hours before a noticeable color change will occur.

Accordingly, there is a need for a sensor which accurately, simply and rapidly detects the presence of biogenic amines in fluids such as food products and body fluids.

SUMMARY OF THE INVENTION

In accordance with the present invention, a polymeric sensor is provided which exhibits selective binding affinity for biogenic amines and undergoes a detectable change in absorption or emission of electromagnetic radiation upon exposure to the biogenic amine. Upon contact with biogenic amine, such as, for example, putrescine (1, 4-diaminopentane), cadaverine (1,5 diaminopentane) and/or histamine (2-(1H-imidazol-4-yl)-ethylamine), the polymer typically undergoes a detectable color change from yellow/green to crimson/purple. The polymer can be formed by the steps comprising:

(a) providing a four-coordinate macrocyclic transition metal complex of the general formula:

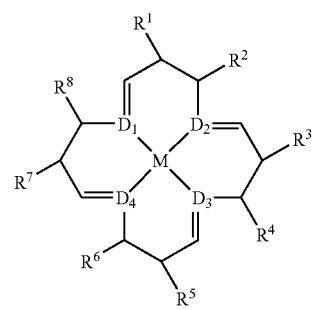

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, respectively, taken together with the adjacent carbon atoms to which they are bonded are joined together to form the same or different group selected from an aromatic or a cyclic group with at least one of the aromatic or cyclic groups possessing one or more polymerizable moieties;

(b) copolymerizing the transition metal complex of step (a) with monomer and optional crosslinking agent to form a polymer which exhibits selective binding affinity for biogenic amine and undergoes a detectable color change when the target molecule binds thereto.

In another embodiment, in step (a) the four-coordinate macrocyclic transition metal complex is reacted with a target molecule comprising at least one biogenic amine to provide a reaction product possessing four or six-coordinate geometry. For example, when the transition metal is nickel (II) and palladium (II), the reaction product will possess four coordinate geometry whereas when the transition metal is iron (II), the reaction product will possess six coordinate geometry. This reaction product, monomer and optional crosslinking agent are then copolymerized using conventional techniques to produce a polymer. Thereafter, the target molecule is removed from the polymer to provide a molecularly imprinted polymer which exhibits selective binding affinity for the target molecule and undergoes a detectable color change when the target molecule binds thereto.

The color change may be in the UV, visible or near infrared region or some combination thereof and will occur to an extent dependent upon the concentration of biogenic amine to which the polymer is exposed. For food spoilage applications, significant color change will take place when the polymer is exposed to about 20 ppm or more of biogenic amine.

The polymer of the present invention can be employed by itself or as a sensor to monitor the presence of biogenic amine in food products, particularly meats and fish, or body fluids on a spot or continuous basis. For example, the polymer can be easily incorporated into common food containers to provide an easily detectable indication of probable spoilage of the food contents within the container.

In another embodiment of the present invention, a sensor for detecting the presence of biogenic amine in, on or in association with a food is provided comprising the foregoing polymer and a support structure having a surface, said polymer being attached to said support structure as a coating thereon. In one embodiment the support structure is a plastic sheet, film or tray which is utilized in the packaging of food products.

Yet another embodiment of the present invention is a method for detecting a biogenic amine, comprising:

exposing the polymer of this invention to a food product, e.g., meat or fish, or body fluid; and, detecting any change in color by the polymer, said detected change being indicative of the presence of biogenic amine in, on or in association with the food product or body fluid.

Still yet another embodiment of the present invention is a device for detecting the presence of a biogenic amine in a fluid, the device comprising:

(a) a compartment having an inlet traversed by the fluid;

(b) a filtration unit mounted in the compartment downstream from the inlet and configured to filter out impurities in the fluid from the biogenic amine; and, (c) a biogenic amine-detecting material located in at least a portion of the compartment downstream from the filter to indicate the presence of the biogenic amine wherein said biogenic amine-detecting material undergoes a detectable color change upon exposure to a biogenic amine.

Further in accordance with the present invention, a portable test kit, suitable for field use, is provided for conducting tests to detect the presence of a biogenic amine containing the foregoing device.

BRIEF DESCRIPTION OF THE DRAWINGS

Other objects, features and advantages of the present invention will occur to those skilled in the art from the following description of preferred embodiments and the accompanying drawings, in which.

DESCRIPTION OF THE PREFERRED EMBODIMENTS

Figure 1:
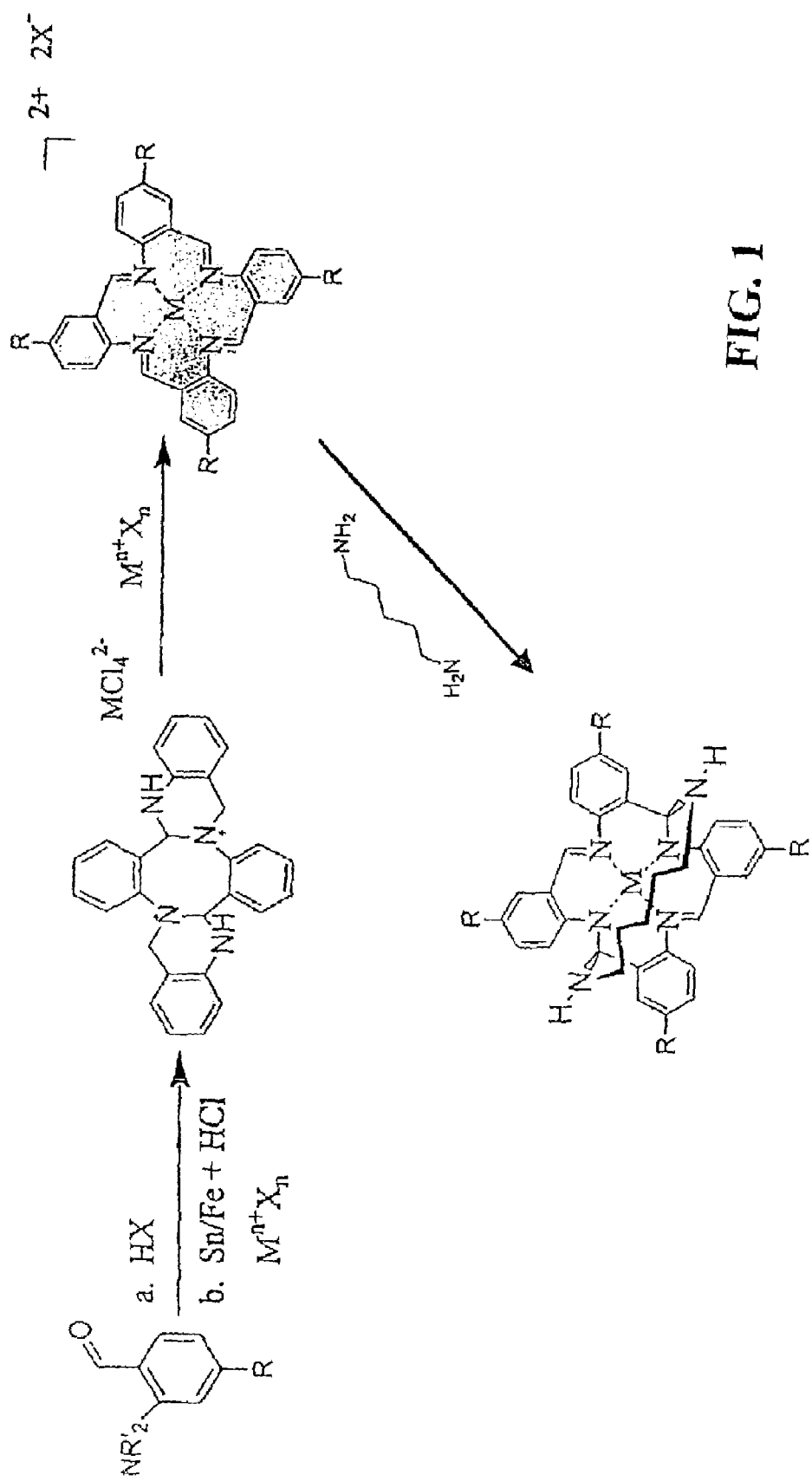
FIG. 1 is a chemical reaction scheme that can be employed to synthesize a polymerizable four-coordinate, yellow colored polymacrocyclic transition metal complex of the present invention.

References cited throughout this written description are incorporated herein in their entirety to more fully describe the state of the art to which they pertain.

As used herein, the phrase "polymeric sensor" or the term "sensor" refers to the polymer disclosed herein as well as the polymer in combination with one or more substrates or devices. As used herein the phrase "molecularly imprinted polymer" refers to a molecular mold-like structure that has preorganized interactive moieties complementing the shape and electronic properties of a target molecule comprising a biogenic amine, such as, for example, putrescine, cadaverine and histamine. The interactive moieties are macrocyclic transition metal complexes possessing a geometrical organization which imparts selective binding characteristics for the biogenic amine. The term "selective binding" is intended to refer to preferential and reversible binding exhibited by the polymeric sensor herein for spoilage indicating biogenic amine compared to molecules having similar structural features and that are present in significant quantities in and on food products, e.g., spermine and spermidine biogenic amines that are present in similar concentrations in both fresh and spoiled meat. Selective binding includes both affinity and specificity of the polymer for spoilage indicating biogenic amine.

The origins of molecularly imprinted molecules trace back to the notion of Linus Pauling that the body assembled a new protein complement (i.e., an antibody) by using the foreign intruder as a template. Although it was later determined that this is not how antibodies are selected in vivo, this template concept stimulated significant thought and research. Molecular imprinting creates specific recognition sites in materials, such as polymeric organic materials. Known molecular imprinting techniques involve crosslinking materials in the presence of a functional monomer or mixture of monomers. The template molecule interacts with a complementary portion of a functional monomer or monomers by maximizing covalent ionic, ion-dipole, hydrogen bonding, dipole-dipole, induced dipole or instantaneous dipole-induced dipole (i.e., London dispersion) attractive interactions, and minimizing coulombic and steric repulsive interactions. In such a way, molecular level recognition sites for the template molecule can be provided in the substrate material. The template molecule is then removed from the substrate to leave a "cavity" or recognition site. Linus Pauling reasoned that shape specificity was obtained by using a target antigen to arrange the complementary shape of an antibody. Thus, a nonspecific molecule can be shaped to the contours of a specific target, and when the target is removed, the shape is maintained to give the antibody a propensity to rebind the antigen. This process is known as "molecular imprinting" or "templating."

Methods for preparing MIPs are described in U.S. Pat. Nos. 4,406,792, 4,415,655, 4,532,232, 4,935,365, 4,960,762, 5,015,576, 5,110,883, 5,208,155, 5,310,648, 5,321,102, 5,372,719, 5,786,428, 6,063,637, and 6,593,142, the contents of which are incorporated by reference herein.

An MIP in accordance with the principles of the present invention can be prepared by the steps which comprise:

(a) providing the reaction product of (i) a four-coordinate macrocyclic transition metal complex of the general formula

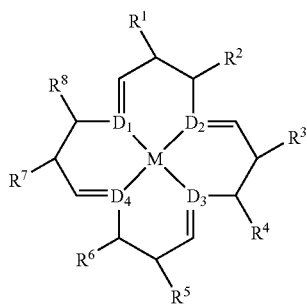

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, respectively, taken together with the adjacent carbon atoms to which they are bonded are joined together to form the same or different group selected from an aromatic or a cyclic group with at least one of the aromatic or cyclic groups possessing one or more polymerizable moieties;

(b) copolymerizing the reaction product of step (b) with monomer and crosslinking agent to form a polymer; and, (c) removing the target molecule from the polymer to provide a molecularly imprinted polymer which exhibits selective binding affinity for the target molecule and undergoes a detectable color change when the target molecule binds thereto. The polymerization reaction mixture for the preparation of the MIP therefore constitutes the reaction product of step (a), one or more polymerizable monomers, one or more (optional) crosslinking agents to impart a sufficiently rigid structure to the polymer end-product (where desired), solvent, and a polymerization initiator. As one skilled in the art would readily appreciate, more than one monomer and/or crosslinking agent can be used in the polymerization method.

The macrocyclic transition metal complex of the present invention corresponds to the formula:

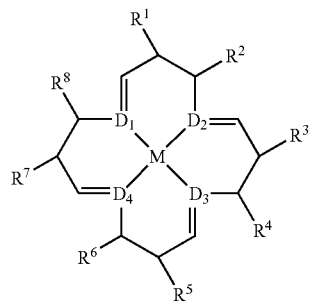

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, respectively, taken together with the adjacent carbon atoms to which they are bonded are joined together to form the same or different group selected from an aromatic or a cyclic group with at least one of the aromatic or cyclic groups possessing one or more polymerizable moieties. Useful aromatic groups possessing a polymerizable moiety which $R^1$ and $R^2$, $R^3$ and $R^4$, $R^5$ and $R^6$, and $R^7$ and $R^8$, respectively, can form when taken together with the adjacent carbon atoms to which they are bonded and joined together includes, for example, benzene rings, naphthalene rings, anthracene rings, phenanthrene rings, thiophene rings and the like. Preferably, $R^1$ and $R^2$, together with the adjacent carbon atoms to which they are bonded are joined together to form a benzene ring. It is also preferred for each of $R^3$ and $R^4$, $R^5$ and $R^6$, and $R^7$ and $R^8$, together with the adjacent carbon atoms to which they are bonded are joined together to form benzene rings. Useful cyclic groups in which $R^1$ and $R^2$, $R^3$ and $R^4$, $R^5$ and $R^6$, and $R^7$ and $R^8$ can form when taken together with the adjacent carbon atoms to which they are bonded and joined together includes, for example, cyclic group containing from 4 to about 20 carbon atoms and optionally having a hetero atom selected from nitrogen, oxygen and sulfur atoms. Specific examples of the cyclic groups include, but are not limited to, cyclobutane, cyclopentane, cyclohexane, cycloheptane, cyclooctane, furan, pyrrole, pyrazole, pyridine, piperidene, piperazine, morpholine, quinoline and the like.

Preferred are macrocyclic compounds corresponding to the general formula

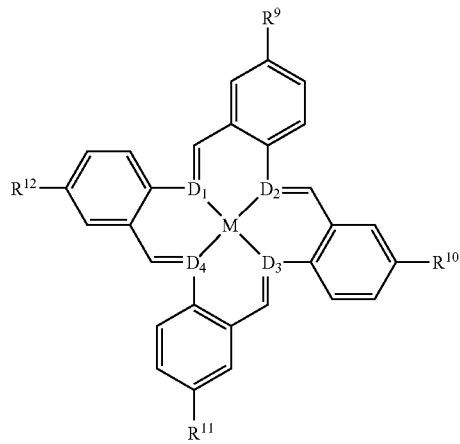

wherein M is nickel(II), palladium(II) or iron (II), $D_1$, $D_2$, $D_3$, and $D_4$ are N, and $R^9$, $R^{10}$, $R^{11}$ and $R^{12}$ are styryl, vinyl, amine, carboxyl, hydroxyl, halomethyl, dithioester, carboxylic acid, acid chloride, and peroxy.

Methods for synthesizing the macrocyclic compounds of the present invention are known. Representative of these methods are those disclosed in, e.g., Kolchinski, Alexander G. et al.,*J. Org. Chem.* 1998, 63, 4515-4517; Kang et al., Novel discotic mesogen: synthesis and liquid crystalline behavior of TAAB (tetrabenzo[b,f,j,n][1,5,9,13]tetraazacyclohexadecine derivatives with long alkoxy chains", *Chem. Commun.*, 1999, pp. 93-94 and U.S. Pat. No. 4,001,212, the contents of which are incorporated by reference herein. The synthesis of a preferred macrocycle, i.e., the metal tetrabenzo[b,f,j,n][1,5,9,13]tetraazacyclohexadecine complex is illustrated in FIG. 1. Alternatively, the preferred macrocycle can be obtained by reacting tetrabenzo[b,f,j,n][1,5,9,13] tetraazacyclohexadecine in a one-to-one ratio with a transition metal salt, e.g., nickel (II) or palladium (II) under conventional reaction conditions. The polymerizable functional groups may take a variety of forms although examples may be selected from the group consisting of styrene, methacrylate, acrylate, vinyl, vinyl ether, vinyl acetate, amine, carboxyl, hydroxyl, trialkoxysilane, dialkoxysilane and epoxy, to form the derivatized nickel(II) complex of tetraazacyclohexadecine which is substituted by polymerizable R groups at the 5 positions on benzene rings of the macrocycle. It will be apparent to those skilled in the art that alternate pathways to synthesizing the product depicted in FIG. 1 are possible.

A wide variety of monomers may be used for synthesizing the polymer sensor in accordance with the principles of the present invention. Preferred monomers include methyl methacrylate, and styrene. Examples of other suitable monomers include all molecules capable of undergoing addition or condensation polymerization. This class includes, but is not limited to, those described in the references cited in this written description and incorporated by reference herein. Further suitable non-limiting examples of monomers that can be used for preparing a polymer of the present invention include methylmethacrylate, other alkyl methacrylates, alkylacrylates, ally or aryl acrylates and methacrylates, cyanoacrylate, styrene, alpha-methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-.alpha.-acryloxy-.beta., .beta.'-dimethyl-g-butyrolactone; N-acryloxy succinimide N-acryloxy-tri.s(hydroxymethyl) aminomethane; N-acryloly chloride; N-acryloyl pyrrolidinone; N-acryloyl-tris(hydroxymethyl) amino methane; 2-amino ethyl methacrylate; N-(3-aminopropyl)methacrylamide; (o, m, or p)-amino-styrene; t-amyl methacrylate; 2-(1-aziridinyl)ethyl methacrylate; 2,2'-azo-bis-(2-amidinopropane); 2,2'-azobisisobutyronitrile; 4,4'-azobis-(4-cyanovaleric acid); 1,1'-azobis-(cyclohexanecarbonitrile); 2,2'-azobis-(2,4-dimethylvaleronitrile); 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl) acrylic acid; 8-bromo-1-octene; 5-bromo-1-pentene; cis-1-bromo-1-propene; .beta.-bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2ol; 3-butenyl chloroformate; 2-butylacrolein; N-t-butylacrylamide; butyl acrylate; butyl methacrylate; (o,m,p)-bromostyrene; t-butyl acrylate; (R)-carvone; (S)-carvone; (−)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1, 1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2, 6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3pentadiene; 2,2-dimethyl-4-pentenal; 2,4-dimethylstyrene; 2,5-dimethylstryene; 3,4dimethylstryene; divinyl benzene; 1,3-divinyltetramethyl disiloxane; 8,13-divinyl-3,7,12,17-tetramethyl-21 H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10,-tetraoraspiro[5,5]undecane; divinyl tin dichloride; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymnethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; lead (II) acrylate; (±)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2(methacryloyloxy)ethyl acetoacetate; (3-methacryloxypropyl)trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrite; 2-methylene-1,3propanediol; 3-methyl-1,2-butadiene; 2-methyl-1-butene; 3-methyl-1-butene; 3-methyl-1buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; alpha.-methyl styrene; t-a-methylstyrene; t-.beta.-methylstyrene; 3-methylstyrene; methyl vinyl ether; methyl vinyl ketone; methyl-2-vinyloxirane; 4-methylstyrene; methyl vinyl sulfonee; 4-methyl5-vinylthiazole; myrcene; t-.beta.-nitrostyrene; 3-nitrostyrene; 1-nonadecene; 1,8-nonadiene; 1octadecene; 1,7-octadiene; 7-octene-1,2-diol; 1-octene; 1-octen-3-ol; 1-pentadecene; 1pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; tetramethyldivinyl siloxane; trans 3-chloroacrylic acid; 2-trifluoromethyl propene; 2-(trifluoromethyl)propenoic acid; 2,4,4'-trimethyl-1-pentene; 3,5-bis (trifluoromethyl)styrene; 2,3-bis(trimethylsiloxy)-1,3butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N(p-vinyl benzyl)-N,N'-dimethyl amine; 4-vinyl biphenyl (4-phenyl styrene); vinyl bromide; 2vinyl butane; vinyl butyl ether; 9-vinyl carbazole; vinyl carbinol; vinyl cetyl ether; vinyl chloroacetate; vinyl chloroformate; vinyl crotonoate; vinyl cyclohexane; 4-vinyl-1cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbomene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2pyrrolidinone; 2-vinyl quinoline; 1-vinyl silatrane; vinyl sulfone; vinyl sulfone (divinylsulfone); vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2methoxyethoxy)silane; vinyl 2-valerate and the like.

Acrylate-terminated or otherwise unsaturated urethanes, carbonates, and epoxies can also be used in the polymer. An example of an unsaturated carbonate is allyl diglycol carbonate (CR-39). Unsaturated epoxies include, but are not limited to, glycidyl acrylate, glycidyl methacrylate, allyl glycidyl ether, and 1,2-epoxy-3-allyl propane.

Crosslinking agents, i.e., monomers that possess two or more polymerizable functional groups, that impart rigidity to the polymer are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bisphenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, and the like.

While free radical polymerization is preferred, monomers can also be selected that are polymerized cationically or anionically. Polymerization conditions should be selected that do not adversely affect the analyte binding site. Any photochemical, radiation chemical, or thermal free radical initiator known to those skilled in the art for free radical polymerization can be used to initiate this method. Examples of UV and thermal initiators include benzoyl peroxide, acetyl peroxide, lauryl peroxide, azobisisobutyronitrile (AIBN), t-butyl peracetate, cumyl peroxide, t-butyl peroxide, t-butyl hydroperoxide, bis(isopropyl)peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2dimethyoxy-2-phenyl-acetophenone, and phenothiazine, and diisopropylxanthogen disulfide.

The choice of monomer and cross-linking agent will be dictated by the chemical (hydrophilicity, chemical stability, degree of cross-linking, ability to graft to other surfaces, interactions with other molecules, etc.) and physical (porosity, morphology, mechanical stability, etc.) properties desired for the polymer. The procedures and conditions which are used to copolymerize the macrocyclic transition metal complex, monomers and cross-linking agent are conventional. The amounts of macrocyclic compound, monomer and crosslinking agents should be chosen to provide a crosslinked polymer exhibiting the desired structural integrity, porosity and hydrophilicity. The amounts can vary broadly, depending on the specific nature/reactivities of the macrocyclic compound, monomer and crosslinking agent chosen as well as the specific sensor application and environment in which the polymer/sensor will be ultimately employed. The relative amounts of each reactant can be varied to achieve desired concentrations of macrocyclic transition metal complexes in the polymer support structure. Typically, the amount of macrocyclic compound will be on the order of about 0.5 to about 1.5 mole percent of monomer. The solvent, temperature, and means of polymerization can be varied in order to obtain polymeric materials of optimal physical or chemical features, for example, porosity, stability, and hydrophilicity. The solvent will also be chosen based on its ability to solubilize all the various components of the reaction mixture.

Polymerizations are generally conducted in bulk solution by the free-radical method. Similar methodology can be applied to surface grafting and particle coating with the polymer, as described in "Surface Grafting of Functional Polymers to Macroporous Poly Trimethylolpropane Trimethacrylate," P. K. Dhal, S. Vidyasankar and F. H. Arnold, *Chemistry of Materials* 7, 154-162 (1995) and "Molecularly-Imprinted Polymers on Silica: Selective Supports for High Performance Ligand-Exchange Chromatography," S. D. Plunkett and F. H. Arnold, *J. Chromatogr. A* 708, 19-29 (1995).

For bulk polymerization, typically about 0.5 to about 1.5 mol percent of the polymerizable macrocyclic compound, about 90 to about 99 mol percent monomer and about 1.0 to about 10 mol percent cross-linker, and about 1 mol percent of a free radical initiator such as 2,2'-azobis(isobutyronitrile) are dissolved in an organic solvent. The reaction solution is placed under an inert atmosphere and heated to a temperature of about 60° C. for a time period of about 2 to about 72 hours.

Polymerizations can also be carried out by a sol-gel process when an alkoxysilane-type of polymerizable compound is used. In this case, the alkoxysilane substituted macrocyclic metal ion complex monomer is hydrolyzed with, for example, tetramethoxysilane,tetraethoxysilane, or poly(glyceryl silicate) in a suitable solvent (see for example, Louloudi, M.; Deligiannakis, Y.; Hadjiliadis, N. *Inorg. Chem.* 1998, 37, 6847-6851; Katz, A.; Davis, M. E. *Nature* 2000, 403, 286; Kloster, G. M.; Taylor, C. M.; Watton, S. P. *Inorg. Chem.* 1999, 38, 3954-3955). The sol-gel condensation can be conducted in acidic or basic conditions using procedures well known to those practiced in the art.

The morphology and selectivity of the polymer for binding the target molecule may be improved by altering the solvent, polymerization temperature, and choice of crosslinking agent, as described in Sellergren, B., Shea, K. J., "Influence Of Polymer Morphology On The Ability Of Imprinted Network Polymers To Resolve Enantiomers," *J. Chromatogr.A* 1993, 635:31-40.

Figure 2:
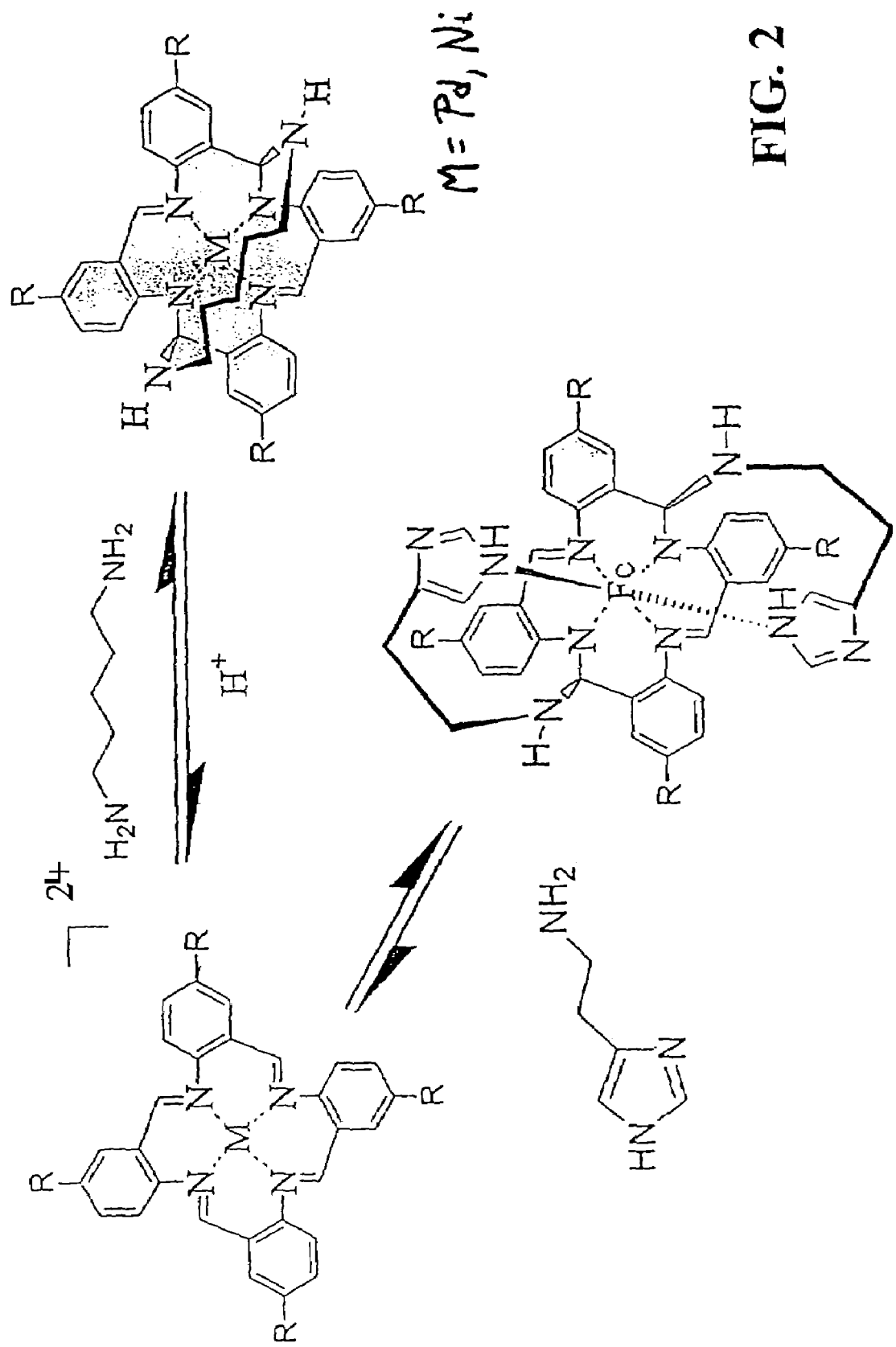
FIG. 2 depicts a chemical equilibrium reaction scheme between a polymerizable four-coordinate, yellow-colored macrocyclic transition metal complex and diamine to produce a four coordinate and a six-coordinate, crimson-colored reaction product.

Removal of the target molecule leaves a macroporous polymer with complementary molecular cavities which include macrocyclic transition metal complexes that have specific binding affinity for biogenic amine. See FIG. 2. The target molecule comprising biogenic amine may be dissociated from the metal ion complex binding site within the polymer by extraction into acidified water.

The polymer of the invention can be prepared in a wide variety of forms ranging from powders to beads to macro structures such as, for example, films, plates, rods, membranes or coatings or other materials. A wide range of sensors can be produced from the polymer of the invention, and the type of sensor will depend on the conditions of use (e.g., spot monitoring, continuous monitoring, process monitoring, whether used during processing, packaging or storage of food, whether used at point of sale or at home, etc.).

The polymer can be easily incorporated into common food containers to provide a quick and easily detectable indication of probable deterioration of the food contents within the container.

Therefore, this invention provides a sensor for detecting the presence of biogenic amines in a food which comprises the polymer. In one embodiment the sensor is a self supporting film placed under the (transparent) packaging material. In another embodiment, the sensor serves as, or is a portion of, the packaging material. The sensor may include a support structure having a surface, said polymer being attached to said support structure as a coating thereon. In one embodiment the support structure is a plastic sheet, film or tray which is utilized in the packaging of food products.

The invention also provides a method for detecting food spoilage, comprising: exposing the polymer of this invention to an environment containing meat or fish such that fluids, i.e., vapors and/or liquids, from the meat or fish come in contact with the polymer, anddetecting any change in color by the polymer, said detected change being indicative of the presence of biogenic amine in, on or in association with said meat or fish.

In one embodiment, the sensor comprises a simple calorimetric indicator, e.g., stick or strip, in which exposure to biogenic amine would result in a visual color change from (1) yellow to crimson when the transition metal ion is nickel (II) or iron (II) or (2) green to purple when the transition metal ion is palladium (II). The scope of the invention is not limited to any one particular type of indicator. For example, U.S. Pat. Nos. 2,485,566, 3,067,015, 4,003,709, 4,285,697, 5,306,466, 5,439,648 and 5,653,941, the contents of which are incorporated by reference herein, all disclose food spoilage indicators for use in packages which may find application in the present invention.

In another embodiment, the change in color of the polymer is detected by a spectroscopic method, such as measurement of the transmittance and/or reflectance spectra, suitably employing fiberoptics and or microelectronic devices.

The change may be detected by removing a sample of fluid from the environment in which biogenic amine may be present for detection, for example, spectroscopically. Preferably, the monitoring is carried out in situ, for example, by providing the polymer of the invention on the packaging or adjacent the foodstuff to be monitored, suitably by using a fiber light guide to and from the polymer to enable detection by remote measurement, or by a small electronic device. Alternatively, an optical fiber may be itself coated with the polymer and, if necessary, the coating sealed with a further coating layer of transparent or translucent polymeric material. Such an optical fiber may, for example, be mounted within a storage refrigerator to enable detection in situ of a color change resulting from spoilage of stored foodstuffs. It is envisioned therefore that optical fibers or microelectronic devices, or a network thereof, may be used in connection with commercial refrigeration plants, to enable continuous monitoring of the contents of the plants.

Therefore, according to a further aspect of the invention, there is provided an apparatus suitable for use in the monitoring method as described above comprising a source of electromagnetic radiation of wavelength covering the region in which the change is to be detected, means for transmitting such radiation to biogenic amine, means for exposing the biogenic amine to the environment to be monitored and means for detecting a change in absorption or reflection of the electromagnetic radiation due to the association of a biogenic amine with the polymer sensor. Such an apparatus is disclosed in U.S. Pat. No. 5,663,072, the contents if which are incorporated by reference herein.

In accordance with yet another aspect of the present invention, there is provided a fluorescent sensor which includes a macrocyclic transition metal complex with conjugate bases of a fluorescent agent compound such as fluorophores as counterions, e.g., 9-anthracenecarboxylic acid, 1-naphthoic acid, carboxylic acid containing fluoresceins, such as, for example, 4',5'-dibromofluorescein, diiodofluorescein, etc., flavianic acid hydrate, phenol red, etc. Upon reaction of the fluorescent macrocycle with a biogenic amine such as cadaverine, the fluorescent agent compound is released and a change in color of the complex will be observed. The released fluorescent agent compound will continue to be transported by the carrier solution into a sensing cavity. The fluorescent agent compound will be excited by a light source, e.g., an LED, and the resulting fluorescence can be detected by a sensor tuned to the wavelength of the fluorescent agent compound emission. In general, the fluorescent agent will act as a counterion to the $MTAAB^{2+}$, much like chloride or tetraflouroborate. The anions of the metal complexes used herein ($MTAAB^{2+}$) can be easily exchanged and is within the purview of one skilled in the art, e.g., as described in Melson, G A and Busch, D H J. of the American Chemical Society 1964, 86, pp. 4834-4837, the contents of which are incorporated herein by reference. See FIG. 3.

Also within the scope of the invention is a method for detecting the presence of biogenic amine in a fluid, comprising:
  exposing the macrocyclic transition metal complex of this invention to a fluid; and,
  detecting any change in color by the macrocyclic transition metal complex, said detected change being indicative of the presence of biogenic amine in the fluid.

Figure 3:
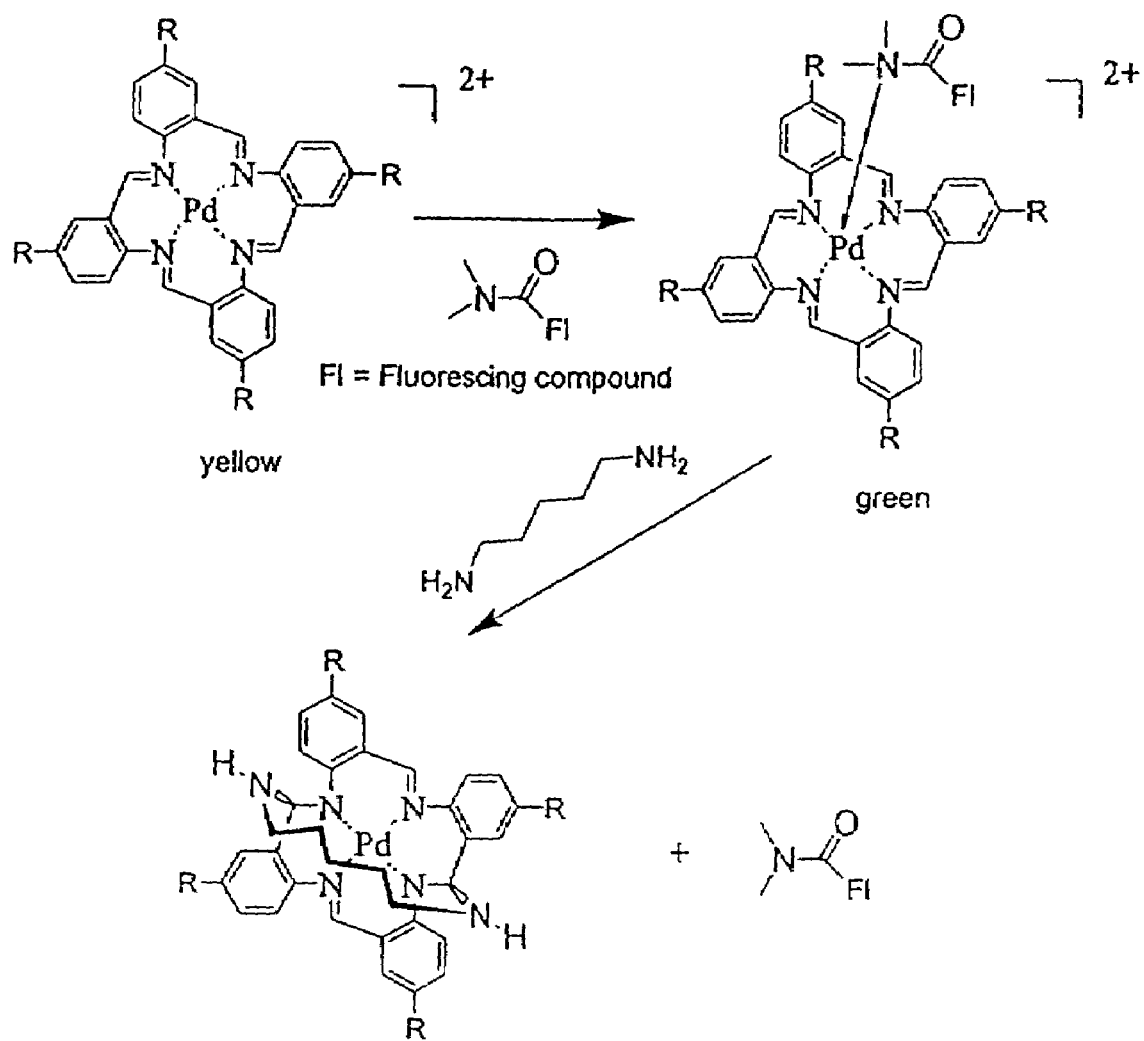
FIG. 3 depicts the chemical reaction scheme illustrating the fluorescent sensor an accordance with the present invention; and, FIG. 4 illustrates a device for detecting the presence of a biogenic amine in a fluid in accordance with the present invention.
Figure 4:
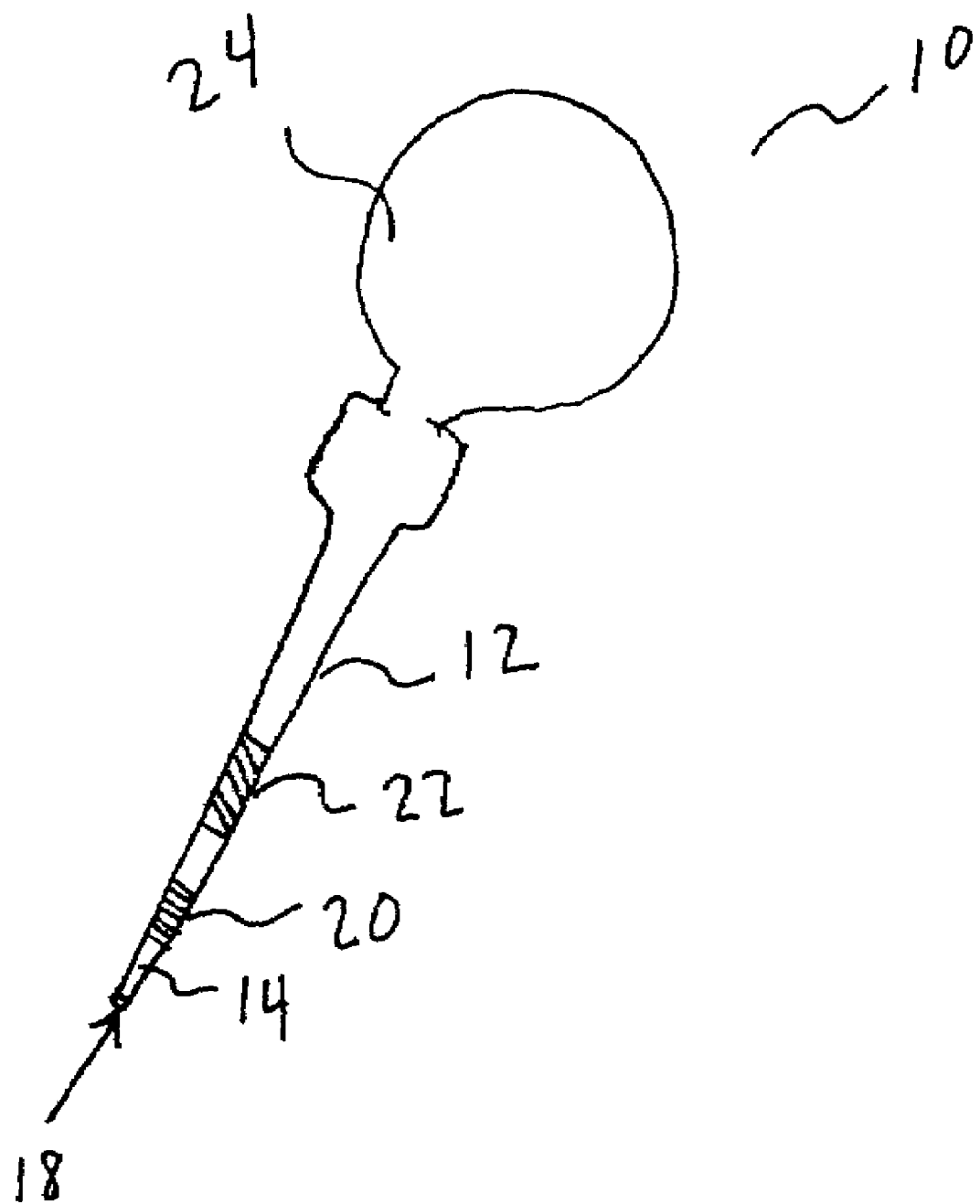

It is further within the scope of the invention to provide a kit containing the apparatus and/or reagents necessary to carry out the foregoing test method in the field. A complete kit would contain all of the equipment and consumables for conducting at least one test procedure. Thus, such a kit would include at least a device for detecting the presence of a biogenic amine in a fluid (vapors and/or liquids) from, e.g., a food product or body fluid such as, for example, vaginal secretions, human urine, etc. As shown in FIG. 3, device 10 would include compartment 12 having an inlet 14 traversed by the fluid 18. Compartment 12 would further include a filtration unit 20 mounted in compartment 12 downstream from inlet 14 and configured to filter out impurities in fluid 18 from the biogenic amine; and a biogenic amine-detecting material 22 located in at least a portion of compartment 12 downstream from filtration unit 20 to indicate the presence of the biogenic amine. In general, the device would further include a means 24 to obtain a test sample of fluid into inlet 14 and compartment 12, e.g., a pipette or syringe for drawing fluid.

Filtration unit 20 can be adjacent to or at a distance from inlet 14 drawing in the fluid and will typically possess a pore size sufficient to filter out impurities from the fluid such as, for example, blood cells, i.e., impurities of at least 1 micron in size. The biogenic amine-detecting material 22 can be obtained by, for example, dissolving the foregoing macrocyclic transition metal complex of the present invention in a suitable solvent, e.g., a polar solvent such as N-methylpyrrolidone or dimethylformamide (DMF), to form a solution, mixing the solution with a substantially colorless inert oxide such as for example, silica gel, titanium dioxide, titania oxide, cellulose and alumina, and evaporating the solvent to provide the inert oxide containing the macrocyclic transition metal complex of the present invention. The device can then be prepared by first placing an amount of the biogenic amine-detecting material in the compartment of the device effective to detect the presence of biogenic amine and then placing the filtration unit therein. These techniques are within the purview of one skilled in the art.

In operation, the device first draws in a fluid downstream in the inlet and though the filtration unit with any impurities in the fluid remaining upstream from the filtration unit. The fluid is then passed downstream from the filtration unit and in contact with the biogenic amine-detecting material. In the case of testing a fluid from a food product, a change in color by the macrocyclic transition metal complex will be indicative of the presence of biogenic amine in the fluid showing that food spoilage has ocurred. In the case of testing a body fluid from a food product, a change in color by the macrocyclic transition metal complex will determine the presence of biogenic amine in the body fluid thus indicating that the patient may be suffering from a disease such as cancer.

Optionally, the kit can also contain a suitable substrate for placing the foregoing macrocyclic transition metal complex of the present invention, e.g., filter paper, such that a sample of a fluid could be placed in contact with the macrocyclic transition metal complex on the filter paper. If any biogenic amine such as cadaverine is present in the fluid, a change in color by the macrocyclic transition metal complex will occur, said detected change being indicative of the presence of biogenic amine in the fluid. To accomplish this, it may be necessary to first mix the macrocyclic transition metal complex with an ionic solvent to suspend the complex and then place the mixture onto the filter paper. Examples of suitable ionic solvents include 1-butyl-3-methylimidazolium tetraflouroborate and those disclosed in http://www.solvent-innovation.de/. Thus, a partial test kit could also include, at a minimum, at least one device for holding a precise volume of macrocyclic transition metal complex and at least one device for holding a precise volume of ionic solvent, filter paper and a device for drawing the fluid and ten dispensing onto the filter paper, e.g., pipette.

As can be appreciated by the skilled artisan, the preferred synthetic schemes and embodiments described above and in the Examples below are not intended to comprise a comprehensive list of all means by which the polymer sensor described and claimed herein may be synthesized. It will be understood that the specified materials and conditions are important in practicing the invention but that unspecified materials and conditions are not excluded so long as they do not prevent the benefits of the invention from being realized. Other suitable methods and starting materials will be evident to those having skill in the art. Additionally, the various synthetic steps described throughout this written description may be performed in an alternate sequence or order to obtain the present invention.

The following non-limiting examples are illustrative of the present invention.

EXAMPLE 1

Synthesis of 5-bromo-2-nitrobenzaldehyde

3-Bromobenzaldehyde (18.5 g, 100 mmol) was added dropwise to a solution of potassium nitrate (20.2 g, 200 mmol) in concentrated sulfuric acid (100 mL) cooled to 0° C. by an ice water bath. The solution was stirred for an additional 15 minutes upon complete addition of 3-bromobenzaldehyde whereupon the entire reaction mixture was added to ice (250 g). The precipitate was isolated by filtration, and the solid was washed with de-ionized water until the pH of the wash was neutral. Drying for 12 hours under vacuum gave the yellow solid, 5-bromo-2-nitrobenzaldehyde was (11.8 g, 51% yield).

EXAMPLE 2

Synthesis of 5-vinyl-2-nitrobenzaldehyde

To a 100 mL Parr reactor Model # 4768 was added 4.6 g, 20 mmol of 5bromo-2-nitrobenzaldehyde of example 1 with dimethylformamide (30 mL), triethylamine (9.1 g, 90 mmol), tri-o-tolyl phosphine (0.060 g, 0.2 mmol), and palladium acetate (0.022 mg, 0.1 mmol). The reactor was charged with ethylene gas (300 psi) and heated to 100° C. for 12 hours. The reactor was then cooled to room temperature and the excess ethylene released. The product, 5-vinyl-2-nitrobenzaldehyde, was recovered by dissolving the reaction mixture in water and washing the aqueous solution with ether (3×50 mL). The combined organic solutions were dried over magnesium sulfate before filtration, followed by removal of the solvent by vacuum. The 5-vinyl-2-nitrobenzaldehyde product was purified by column chromatography with silica gel as stationary phase and chloroform as eluent to give a light brown solid (1.9 g, 53% yield).

EXAMPLE 3

Synthesis of VTAAB $FeCl_4^{2-}$

The precursor macrocycle, tetravinyl-4b,5,15 b, 16-tetrahydrodibenzo[3,4:7,8][1,5]diazocino[2,1-b:6,5-b] diquinazoline-11,22-diium (VTHDDDD), was formed by reaction of 1.9 g (10.7 mmol) of 5-vinyl-2-nitrobenzaldehyde of Example 2 with iron powder (1.86 g, 33.2 mmol), concentrated hydrochloric acid (6 mL), and acetonitrile (6.7 mL) and held at 0° C. or below for 48 hours. The VTHDDDD $FeCl_4^{2-}$ was then isolated by filtration and washed with cold ethanol (2×10 mL) to give a red solid (1.39 g, 73% yield).

EXAMPLE 4

Synthesis of PdVTAAB Macrocycle Complex

Into a 250 mL flask was added 0.5 g (0.7 mmol) of the VTHDDDD $FeCl_4^{2-}$ of Example 3, ethanol (100 mL) and dichloro bis(acetonitrile) palladium (0.18 g, 0.7 mmol). The reaction solution was heated to reflux and palladium tetravinyltetrabenzo[b,f,j,n] [1,5,9,13] tetraazacylohexadecine (PdVTAAB) precipitated from the reaction solution. The solution volume was reduced to one-quarter of the original amount, cooled to room temperature, and the tan solid was isolated by filtration. PdVTAAB (0.49 g, 67% yield) was used without further purification. When placed in a polar solvent such DMF, the product appears green.

Similarly, the nickel analogue would be synthesized by refluxing the VTHDDDD of Example 3 with nickel acetate in ethanol, while the iron analogue would be synthesized by refluxing the macrocycle precursor of Example 3 in triethylamine.

EXAMPLE 5

Selecto brand silica gel (100 mg, mesh size 63-200) and NiTAAB (2 mg) were placed into a 1.0 mL polystyrene vial with a polyethylene cap and polystyrene ball pestle available from Crescent (Elgin, Ill.). The capped vial was then placed into a Wig-L-Bug ball mill available from Crescent (Elgin, Ill.) and the mixture was homogenized for about one minute under high frequency. The light brown powder was transferred into Millipore ZipTip pipetter tips (100 uL volume, C4 filter resin) available from Fisher Scientific (Pittsburgh, Pa.) and the packed pipetter tips were shaken to fully pack the homogenized silica gel/NiTAAB. Samples of meat fluids were then taken with a Wheaton Acura Micropipetter (Fisher Scientific, 100 uL). A change in the color of NiTAAB indicates whether a biogenic amine is present.

What is claimed is:

1. A polymer comprising the reaction product of:
   (a) a macrocyclic transition metal complex of the general formula:

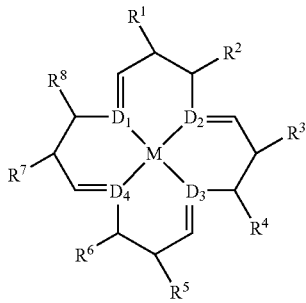

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, taken together with the adjacent carbon atoms to which they are bonded, are joined together to form the same or different group selected from an aromatic or a cyclic group with at least one of the aromatic or cyclic groups possessing one or more polymerizable moieties;
   (b) monomer; and
   (c) optional crosslinking agent,
   wherein said polymer undergoes a detectable color change upon exposure to a biogenic amine.

2. The polymer of claim 1 wherein the aromatic groups to which $R^1$ and $R^2$, $R^3$ and $R^4$, $R^5$ and $R^6$, and $R^7$ and $R^8$ can form when taken together with the adjacent carbon atoms to which they are bonded and joined together are selected from the group consisting of benzene rings, naphthalene rings, anthracene rings, phenanthrene rings, and thiophene rings.

3. The polymer of claim 2 wherein in the macrocyclic transition metal complex M is nickel(II) or palladium (II) and $D_1$, $D_2$, $D_3$, and $D_4$ are N.

4. The polymer of claim 1 wherein in the macrocyclic transition metal complex M is nickel(II) or palladium (II) and $D_1$, $D_2$, $D_3$, and $D_4$ are N.

5. The polymer of claim 1 wherein the biogenic amine is selected from the group consisting of cadaverine, putrescine and histamine.

6. The polymer of claim 1 wherein the a macrocyclic transition metal complex is of the formula:

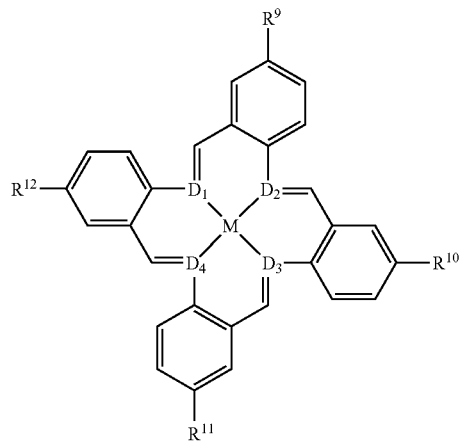

wherein M is nickel(II) or palladium(II), $D_1$, $D_2$, $D_3$, and $D_4$ are N, and $R^9$, $R^{10}$, $R^{11}$ and R 12 are styrene, vinyl, amine or carboxyl.

7. A food container comprising the polymer of claim 1.

8. A molecularly imprinted polymer formed by the steps of:
   (a) providing the reaction product of (i) a four-coordinate a macrocyclic transition metal complex of the general formula:

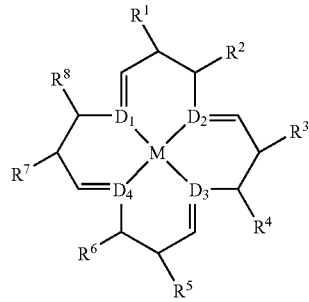

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, taken together with the adjacent carbon atoms to which they are bonded, are joined together to form the same or different group selected from an aromatic or a cyclic group with at least one of the aromatic or cyclic groups possessing one or more polymerizable moieties, and (ii) a target molecule comprising biogenic amine, said reaction product possessing a four or six-coordinate geometry;
   (b) copolymerizing the reaction product of step (a) with monomer and crosslinking agent to form a polymer; and
   (c) removing the target molecule from the polymer to provide a molecularly imprinted polymer which selectively binds to the target molecule and undergoes a detectable color change when the target molecule binds thereto.

9. The molecularly imprinted polymer of claim 8 wherein the aromatic groups to which $R_1$ and $R_2$, $R_3$ and $R_4$, $R_5$ and $R_6$, and $R_7$ and $R_8$ can form when taken together with the adjacent carbon atoms to which they are bonded and joined together are selected from the group consisting of benzene rings, naphthalene rings, anthracene rings, phenanthrene rings, and thiophene rings.

10. The molecularly imprinted polymer of claim 8 wherein in the macrocyclic transition metal complex M is nickel(II) or palladium (II) and $D_1$, $D_2$, $D_3$, and $D_4$ are N and wherein the reaction product formed in step (a) possesses a four coordinate geometry.

11. The molecularly imprinted polymer of claim 8 wherein in the macrocyclic transition metal complex M is iron (II) and $D_1$, $D_2$, $D_3$, and $D_4$ are N and wherein the reaction product formed in step (a) possesses a six coordinate geometry.

12. The molecularly imprinted polymer of claim 8 wherein the biogenic amine is selected from the group consisting of cadaverine, putrescine and histamine.

13. The molecularly imprinted polymer of claim 8 wherein the a macrocyclic transition metal complex is of the formula:

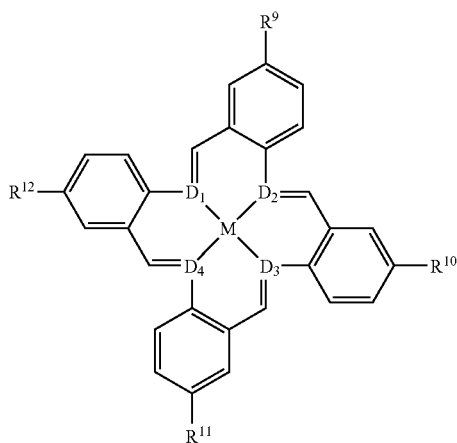

wherein M is nickel(II), palladium(II) or iron (II), $D_1$, $D_2$, $D_3$, and $D_4$ are N, and $R^9$, $R^{10}$, $R^{11}$ and $R^{12}$ are styryl, vinyl, amine, carboxyl, hydroxyl, halomethyl, dithioester, carboxylic acid, acid chloride or peroxy.

14. A food container comprising the polymer of claim 8.

15. A process for preparing a polymer comprising:
copolymerizing a macrocyclic transition metal complex of the general formula:

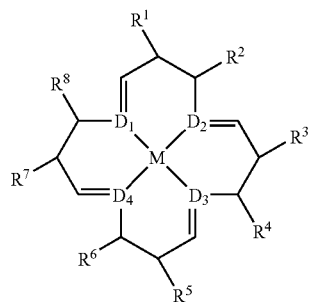

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, taken together with the adjacent carbon atoms to which they are bonded, are joined together to form the same or different group selected from an aromatic or a cyclic group with at least one of the aromatic or cyclic groups possessing one or more polymerizable moieties, monomer and optional crosslinking agent, wherein said polymer undergoes a detectable color change upon exposure II to a biogenic amine.

16. The process of claim 15 wherein the aromatic groups to which $R^1$ and $R^2$, $R^3$ and $R^4$, $R^5$ and $R^6$, and $R^7$ and $R^8$ can form when taken together with the adjacent carbon atoms to which they are bonded and joined together are selected from the group consisting of benzene rings, naphthalene rings, anthracene rings, phenanthrene rings, and thiophene rings.

17. The process of claim 16 wherein in the macrocyclic transition metal complex M is nickel(II), palladium (II) or iron (II) and $D_1$, $D_2$, $D_3$, and $D_4$ are N.

18. The process of claim 15 wherein in the macrocyclic transition metal complex M is nickel(II), palladium (II) or iron (II) and $D_1$, $D_2$, $D_3$, and $D_4$ are N.

19. The process of claim 15 wherein the biogenic amine is selected from the group consisting of cadaverine, putrescine and histamine.

20. The process of claim 15 wherein the a macrocyclic transition metal complex is of the formula:

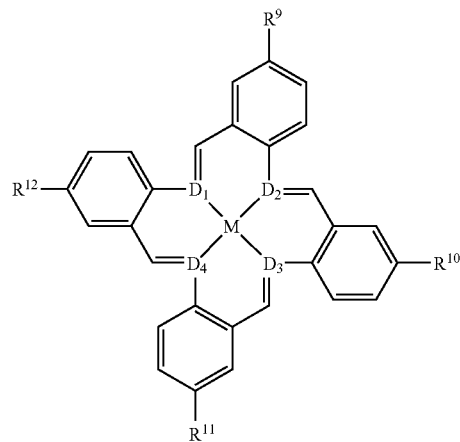

wherein M is nickel(II), palladium(II) or iron (II), $D_1$, $D_2$, $D_3$, and $D_4$ are N, and $R^9$, $R^{10}$, $R^{11}$ and $R^{12}$ are styryl, vinyl, amine, carboxyl, hydroxyl, halomethyl, dithioester, carboxylic acid, acid chloride or peroxy.

21. A process for preparing a molecularly imprinted polymer which comprises:

(a) providing the reaction product of (i) a four-coordinate a macrocyclic transition metal complex of the general formula:

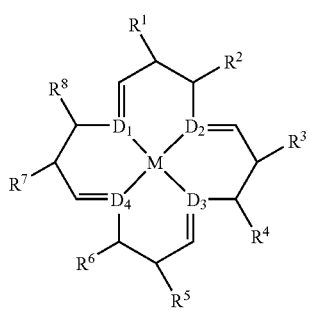

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, taken together with the adjacent carbon atoms to which they are bonded, are joined together to form the same or different group selected from an aromatic or a cyclic group with at least one of the aromatic or cyclic groups possessing one or more polymerizable moieties, and (ii) a target molecule comprising biogenic amine, said reaction product possessing a six-coordinate geometry;

(b) copolymerizing the reaction product of step (A) with monomer and crosslinking agent to form a polymer; and (c) removing the target molecule from the polymer to provide a molecularly imprinted polymer which selectively binds to the target molecule and undergoes a detectable color change when the target molecule binds thereto.

22. The process of claim 21 wherein the aromatic groups to which $R^1$ and $R^2$, $R^3$ and $R^4$, $R^5$ and $R^6$, and $R^7$ and $R^8$ can form when taken together with the adjacent carbon atoms to which they are bonded and joined together are selected from the group consisting of benzene rings, naphthalene rings, anthracene rings, phenanthrene rings, and thiophene rings.

23. The process of claim 22 wherein in the macrocyclic transition metal complex M is nickel(II), palladium (II) or iron (II) and $D_1$, $D_2$, $D_3$, and $D_4$ are N.

24. The process of claim 21 wherein in the macrocyclic transition metal complex M is nickel(II), palladium (II) or iron (II) and $D_1$, $D_2$, $D_3$, and $D_4$ are N.

25. The process of claim 21 wherein the biogenic amine is selected from the group consisting of cadaverine, putrescine and histamine.

26. The process of claim 21 wherein the a macrocyclic transition metal complex is of the formula:

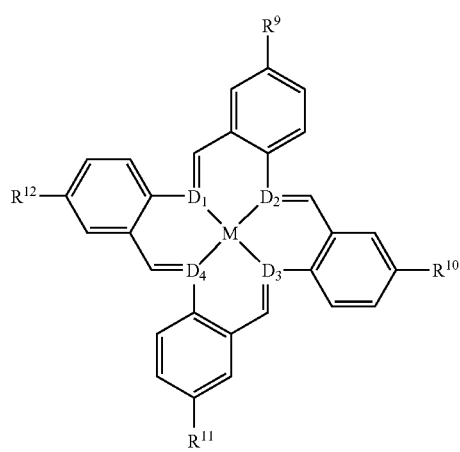

wherein M is nickel(II), palladium(II) or iron (II), $D_1$, $D_2$, $D_3$, and $D_4$ are N, and $R^9$, $R^{10}$, $R^{11}$ and $R^{12}$ are styryl, vinyl, amine, carboxyl, hydroxyl, halomethyl, dithioester, carboxylic acid, acid chloride or peroxy.

27. A sensor for detecting the presence of biogenic amine in, on or in association with a fluid which comprises a polymer and a support structure having a surface, the polymer being attached to the support structure as a coating thereon, wherein the polymer is formed by the steps of: copolymerizing a macrocyclic transition metal complex of the general formula:

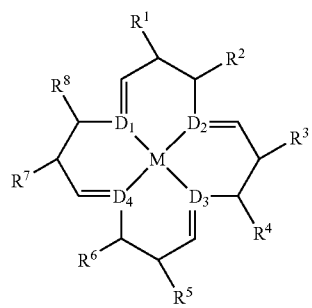

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, taken together with the adjacent carbon atoms to which they are bonded, are joined together to form the same or different group selected from an aromatic or a cyclic group with at least one of the aromatic or cyclic groups possessing one or more polymerizable moieties, monomer and crosslinking agent, wherein said polymer undergoes a detectable color change upon exposure to a biogenic amine.

28. The sensor of claim 27 wherein the structure comprises a plastic sheet, film or tray which is utilized in the packaging of food products.

29. The sensor of claim 27 wherein the structure is an optical fiber.

30. The sensor of claim 27 wherein the biogenic amine is selected from the group consisting of cadaverine, putrescine and histamine.

31. The sensor of claim 27 wherein the macrocyclic transition metal complex is first reacted with a target molecule comprising a biogenic amine prior to copolymerizing the complex, monomer and crosslinking agent, and thereafter the target molecule is removed from the polymer to provide a molecularly imprinted polymer which selectively binds to the target molecule and undergoes a detectable color change when the target molecule binds thereto.

32. The sensor of claim 27 wherein the color change is visible.

33. The sensor of claim 27 wherein the color change is from yellow to crimson when the transition metal ion is nickel (II) or iron (II) and is from green to purple when the transition metal ion is palladium (II).

34. A method for detecting a biogenic amine, comprising: providing a polymer comprising the reaction product of a macrocyclic transition metal complex of the general formula:

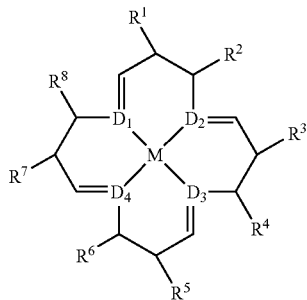

wherein M is a transition metal ion; $D_1$, $D_2$, $D_3$ and $D_4$ can be the same or different and can be N or P; and each of $R^1$ and $R^2$, $R^3$ and $R^4$, $R^5$ and R, and $R^7$ and $R^8$, taken together with the adjacent carbon atoms to which they are bonded, are joined together to form the same or different group selected from an aromatic or a cyclic group with at least one of the aromatic or cyclic groups possessing one or more polymerizable moieties, monomer and crosslinking agent, exposing the polymer to a food product or body fluid; and, detecting any change in color by the polymer, said detected change being indicative of the presence of biogenic amine in, on or in association with the food product or body fluid.

35. The method of claim 34 wherein the aromatic groups to which $R^1$ and $R^2$, $R^3$ and $R^4$, $R^5$ and $R^6$, and $R^7$ and $R^8$ can form when taken together with the adjacent carbon atoms to which they are bonded and joined together are selected from the group consisting of benzene rings, naphthalene rings, anthracene rings, phenanthrene rings, and thiophene rings.

36. The method of claim 34 wherein in the macrocyclic transition metal complex M is nickel(II), palladium (II) or iron (II) and $D_1$, $D_2$, $D_3$, and $D_4$ are N.

37. The method of claim 35 wherein in the macrocyclic transition metal complex M is nickel(II), palladium (II) or iron (II) and $D_1$, $D_2$, $D_3$, and $D_4$ are N.

38. The method of claim 34 wherein the biogenic amine is selected from the group consisting of cadaverine, putrescine and histamine.

39. The method of claim 34 wherein the a macrocyclic transition metal complex is of the formula:

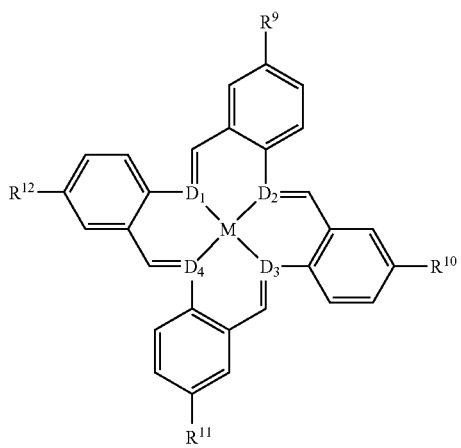

wherein M is nickel(II), palladium(II) or iron (II), $D_1$, $D_2$, $D_3$, and $D_4$ are N, and $R^9$, $R^{10}$, $R^{11}$ and $R^{12}$ are styryl, vinyl, amine, carboxyl, hydroxyl, halomethyl, dithioester, carboxylic acid, acid chloride or peroxy.

40. The method of claim 34 wherein the macrocyclic transition metal complex is first reacted with a target molecule comprising biogenic amine prior to copolymerizing the complex, monomer and crosslinking agent, and thereafter the target molecule is removed from the polymer to provide a molecularly imprinted polymer which selectively binds to the target molecule and undergoes a detectable color change when the target molecule binds thereto.

41. The method of claim 34 wherein the color change is visible.

42. The method of claim 34 wherein the color change is from yellow to crimson when the transition metal ion is nickel (II) or iron (II) and is from green to purple when the transition metal ion is palladium (II).

43. A device for detecting a biogenic amine in a fluid comprising:
(a) a compartment having an inlet traversed by the fluid;
(b) a filtration unit mounted in the compartment downstream from the inlet and configured to filter out impurities in the fluid from the biogenic amine; and,
(c) a biogenic amine-detecting material located in the compartment downstream from the filtration unit to indicate the presence of the biogenic amine wherein said biogenic amine-detecting material undergoes a detectable color change upon exposure to a biogenic amine wherein the biogenic amine-detecting material comprises a macrocyclic transition metal complex of the general formula:

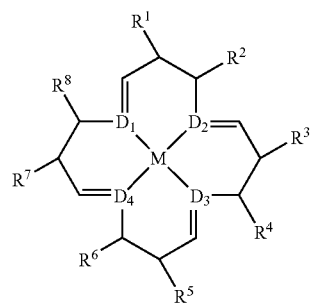

wherein M is a transition metal ion; $D_1$, $D_2$, $D_3$, and $D_4$ can be the same or different and can be N or P; and each of $R^1$, and $R^2$, $R^3$ and $R^4$, $R^5$ and $R_6$, and $R_7$ and $R^8$, taken together with the adjacent carbon atoms to which they are bonded, are joined together to form the same or different group selected from an aromatic or a cyclic group with at least one of the aromatic or cyclic groups possessing one or more polymerizable moieties.

44. The device of claim 43 wherein the filtration unit possesses a pore size to filter impurities greater than one micron.

45. The device of claim 43 wherein the aromatic groups to which $R^1$ and $R^2$, $R^3$ and $R^4$, $R^5$ and $R^6$, and $R^7$ and $R^8$ can form when taken together with the adjacent carbon atoms to which they are bonded and joined together are selected from the group consisting of benzene rings, naphthalene rings, anthracene rings, phenanthrene rings, and thiophene rings.

46. The device of claim 45 wherein in the macrocyclic transition metal complex M is nickel(II), palladium (II) or iron (II) and $D_1$, $D_2$, $D_3$, and $D_4$ are N.

47. The device of claim 43 wherein in the macrocyclic transition metal complex M is nickel(II), palladium (II) or iron (II) and $D_1$, $D_2$, $D_3$, and $D_4$ are N.

48. The device of claim 43 wherein the biogenic amine to be detected is selected from the group consisting of cadaverine, putrescine and histamine.

49. The device of claim 43 wherein the macrocyclic transition metal complex is of the formula:

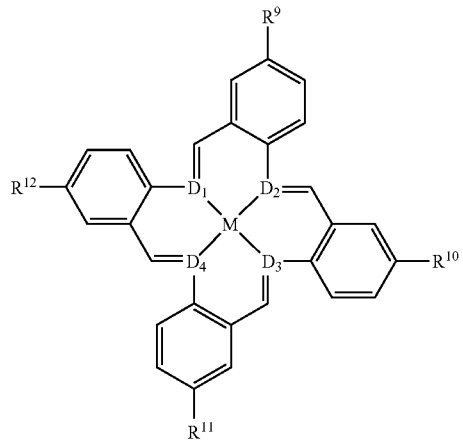

wherein M is nickel(II), palladium(II) or iron (II), $D_1$, $D_2$, $D_3$, and $D_4$ are N, and $R^9$, $R^{10}$, $R^{11}$ and $R^{12}$ are styryl, vinyl, amine, carboxyl, hydroxyl, halomethyl, dithioester, carboxylic acid, acid chloride or peroxy.

50. A test kit for determining the presence or absence of a biogenic amine in a representative sample of fluid, the kit comprising one or more of the devices of claim 49.

51. The device of claim 43 wherein the biogenic amine-detecting material further comprises an inert oxide selected from the group consisting of silica gel, titanium dioxide, titania oxide, cellulose and alumina.

52. The device of claim 51 which is a pipette or a syringe.

53. A test kit for determining the presence or absence of a biogenic amine in a representative sample of fluid, the kit comprising one or more of the devices of claim 51.

54. The device of claim 43 which is a pipette or a syringe.

55. The device of claim 43 wherein the fluid is associated with a food product.

56. The device of claim 43 wherein the fluid is a body fluid.

57. A test kit for determining the presence or absence of a biogenic amine in a representative sample of fluid, the kit comprising one or more of the devices of claim 43.

58. A method for detecting the presence of biogenic amine in a fluid, comprising:

exposing a fluid to a macrocyclic transition metal complex of the general formula:

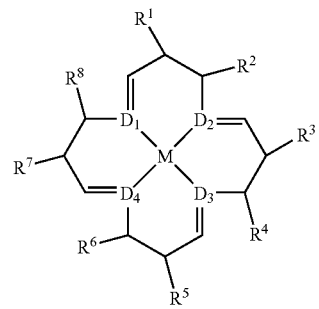

wherein M is a transition metal ion; $D_1$, $D_2$, $D_3$ and $D_4$ can be the same or different and can be N or P; and each of $R^1$ and $R^2$, $R^3$ and $R^4$, $R^5$ and $R^6$, and $R^7$ and $R^8$, taken together with adjacent carbon atoms to which they are bonded, are joined together to form the same or different group selected from an aromatic or a cyclic group with at least one of the aromatic or cyclic groups possessing one or more polymerizable moieties; and, detecting any change in color by the macrocyclic transition metal complex, said detected change being indicative of the presence of biogenic amine in the fluid.

59. The method of claim 58, wherein the aromatic groups to which $R^1$ and $R^2$, $R^3$ and $R^4$, $R^5$ and $R^6$, and $R^7$ and $R^8$ can form when taken together with the adjacent carbon atoms to which they are bonded and joined together are selected from the group consisting of benzene rings, naphthalene rings, anthracene rings, phenanthrene rings, and thiophene rings.

60. The method of claim 59 wherein in the macrocyclic transition metal complex M is nickel(II), palladium (II) or iron (II) and $D_1$, $D_2$, $D_3$, and $D_4$ are N.

61. The method of claim 58 wherein in the macrocyclic transition metal complex M is nickel(II), palladium (II) or iron (II) and $D_1$, $D_2$, $D_3$, and $D_4$ are N.

62. The method of claim 58 wherein the biogenic amine to be detected is selected from the group consisting of cadaverine, putrescine and histamine.

63. The method of claim 58 wherein the macrocyclic transition metal complex is of the formula:

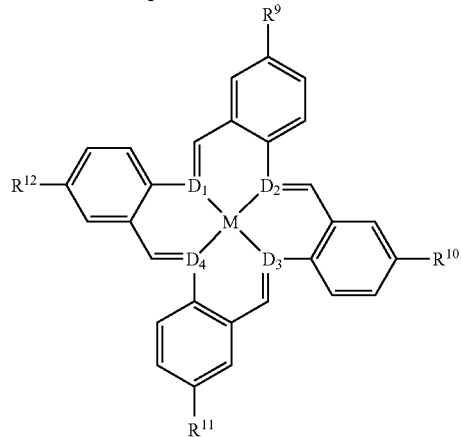

wherein M is nickel(II), palladium(II) or iron (II), $D_1$, $D_2$, $D_3$, and $D_4$ are N, and $R^9$, $R^{10}$, $R^{11}$ and $R^{12}$ are styryl, vinyl, amine, carboxyl, hydroxyl, halomethyl, dithioester, carboxylic acid, acid chloride or peroxy.

64. The method of claim 58 wherein the macrocyclic transition metal complex further comprises conjugate bases of a fluorescent agent compound.

65. The method of claim 64 wherein the fluorescent agent compound is a fluorophore.

66. The method of claim 65 wherein the fluorophore is selected from the group consisting of 9-anthracenecarboxylic acid, 1-naphthoic acid and carboxylic acid containing fluorosceins 67. The method of claim 58 wherein the fluid is associated with meat or fish.

68. The method of claim 58 wherein the fluid is a body fluid.

* * * * *